US012582592B2

(12) United States Patent
Nakasone et al.

(10) Patent No.: US 12,582,592 B2
(45) Date of Patent: Mar. 24, 2026

(54) FLAVOR OR AROMA DETERIORATION INHIBITOR CONTAINING THEANAPHTHOQUINONE AND ANALOGUES THEREOF AS ACTIVE INGREDIENT

(71) Applicant: Ogawa & Co., Ltd., Tokyo (JP)

(72) Inventors: Rie Nakasone, Ibaraki (JP); Toshio Ueno, Ibaraki (JP); Kenji Adachi, Ibaraki (JP); Shuichi Muranishi, Ibaraki (JP); Ai Okamoto, Chiba (JP)

(73) Assignee: OGAWA & CO., LTD., Tokyo (JP)

( * ) Notice: Subject to any disclaimer, the term of this patent is extended or adjusted under 35 U.S.C. 154(b) by 892 days.

(21) Appl. No.: 17/615,665

(22) PCT Filed: Aug. 1, 2019

(86) PCT No.: PCT/JP2019/030230

§ 371 (c)(1),
(2) Date: Dec. 1, 2021

(87) PCT Pub. No.: WO2021/019763

PCT Pub. Date: Feb. 4, 2021

(65) Prior Publication Data

US 2022/0218580 A1 Jul. 14, 2022

(51) Int. Cl.

| | |
|---|---|
| ***A61K 8/49*** | (2006.01) |
| ***A23B 2/771*** | (2025.01) |
| ***A23L 27/12*** | (2016.01) |
| ***A61Q 19/00*** | (2006.01) |

(52) U.S. Cl.

CPC .............. *A61K 8/498* (2013.01); *A23B 2/771* (2025.01); *A23L 27/13* (2016.08); *A61Q 19/00* (2013.01); *A23V 2002/00* (2013.01); *A61K 2800/10* (2013.01); *A61K 2800/524* (2013.01)

(58) Field of Classification Search

CPC .............. A23L 27/13; A23L 2/02; A23L 2/56; A23L 27/2052; A23L 27/84; A61K 2800/10; A61K 2800/524; A61K 8/498; A61K 2800/522; A61K 8/33; A23V 2002/00; A61Q 19/00; A61Q 13/00; A23B 2/771; A23F 3/405

See application file for complete search history.

(56) References Cited

FOREIGN PATENT DOCUMENTS

| | | | |
|---|---|---|---|
| JP | 2002-507887 | 3/2002 | |
| JP | 2002-095415 | 4/2002 | |
| JP | 2002-180081 | 6/2002 | |
| JP | 2002-338990 | 11/2002 | |
| JP | 2003-96486 | 4/2003 | |
| JP | 2004-18613 | 1/2004 | |
| JP | 2005-171116 | 6/2005 | |
| JP | 2005171116 A * | 6/2005 | |
| WO | 98/58656 | 12/1998 | |
| WO | WO-03045328 A2 * | 6/2003 | ........... A61K 31/352 |
| WO | 2009/011271 | 1/2009 | |

OTHER PUBLICATIONS

Jhoo et al (J. Agric. Food Chem. 2005,53, 6146-6150) (Year: 2005).*

Kosinska et al (processing and impact on antioxidants in beverages, 2014) (Year: 2014).*

International Preliminary Report on Patentability issued Feb. 10, 2022 in corresponding International (PCT) Patent Application No. PCT/JP2019/030230.

International Search Report issued Oct. 1, 2019 in International (PCT) Application No. PCT/JP2019/030230.

Patent Office Journal, Collection of Well-known Prior Arts (Fragrances), Part I, General Fragrances, Jan. 29, 1999, pp. 141-147.

Schieberle, P. et al., "Identification of Potent Flavor Compounds Formed in an Aqueous Lemon Oil/Citric Acid Emulsion" J. Agric. Food Chem., 1988, vol. 36, pp. 797-800.

The 57th Natural Organic Compounds Symposium Proceedings, P-33, pp. 375-380, 2015, with English abstract.

Li, Y. et al., "Reaction of the Black Tea Pigment Theaflavin during Enzymatic Oxidation of Tea Catechins", Journal of Natural Products, 2010, vol. 73, No. 1, pp. 33-39.

Jhoo, J-W. et al., "Stability of Black Tea Polyphenol, Theaflavin, and Identification of Theanaphthoquinone as its Major Radical Reaction Product", Journal of Agricultural and Food Chemistry, 2005, vol. 53, pp. 6146-6150.

Tanaka, T. et al., "Two Types of Oxidation Dimerization of the Black Tea Polyphenol Theaflavin", J. Agric. Food Chem., 2001, vol. 49, pp. 5785-5789.

* cited by examiner

*Primary Examiner* — Jean P Cornet

(74) *Attorney, Agent, or Firm* — WENDEROTH, LIND & PONACK, L.L.P.

(57) ABSTRACT

Provided is a deterioration inhibitor which, compared to prior art, is more effective against deterioration of the flavor or aroma of food, drinks, cosmetics, and the like caused by a variety of factors, and does not have any influence on the color of the food, drinks, cosmetics, and the like. This flavor or aroma deterioration inhibitor contains theanaphthoquinone and analogues thereof as an active ingredient.

15 Claims, No Drawings

FLAVOR OR AROMA DETERIORATION INHIBITOR CONTAINING THEANAPHTHOQUINONE AND ANALOGUES THEREOF AS ACTIVE INGREDIENT

TECHNICAL FIELD

The present invention relates to a flavor or aroma deterioration inhibitor that can be widely applied to what people put into their mouths in daily life, for example, food and drinks, oral hygiene agents such as dentifrices, halitosis inhibitors, or pharmaceuticals administered orally (hereinafter collectively referred to as "oral products"), and flavor and fragrance compositions or cosmetic products, and a method for inhibiting deterioration of flavor or aroma.

BACKGROUND ART

In general, the aroma and flavor of food and drinks have a great influence on the increase or diminution of appetite, and therefore the flavor is considered to be an important element in dietary habits as well as various nutritional components. Moreover, the aroma imparted to toiletries such as cosmetics, soap, and shampoo masks the substrate odor and has the effect of providing a pleasant sensation to the user and those therearound, which is an important element in cosmetics and the like.

However, it is well known that many of the flavor or aroma components of food and drinks, cosmetics, and the like are chemically unstable and gradually deteriorate due to oxygen, light, heat, and the like, and the original flavor or aroma is lost at each stage of the production, distribution, storage, and the like, or off-taste and off-odor (deteriorated odor) are generated.

Conventionally, in order to inhibit such deterioration of flavor or aroma, addition of various antioxidants such as ascorbic acid and photodegradation inhibitors has been proposed (Non-Patent Document 1).

Citral has a lemon-like flavor or aroma and is an important component that imparts a citrus feeling and a fresh feeling to products such as food and drinks, cosmetics, and the like.

Citral is known to undergo reactions such as cyclization, oxidation, hydration, and isomerization under acidic conditions to produce various off-flavor (unpleasant flavor) components (Non-Patent Document 2).

Among the off-flavor components, p-methylacetophenone and p-cresol have a particularly strong unpleasant odor and are known to lead to a significant deterioration in product quality.

A p-methylacetophenone production inhibitor in which a plant extract containing rosmarinic acid is used as a stabilizer has been proposed to inhibit production of p-methylacetophenone (Patent Document 1).

Moreover, deteriorated odor production inhibitors of citral characterized by being formed from at least one selected from the group consisting of extracts that are solvent-extracted from Chinese quince, mango, mangosteen, milovalan, pomegranate and cacao, respectively, epicatechin, epicatechin gallate, epigallocatechin gallate, enzyme-treated rutin, quercetin, ferulic acid, caffeic acid, rosmarinic acid, syringa acid, and gallic acid, have also been proposed (Patent Document 2).

Further, a citrus-based flavor composition containing tea polyphenol as a flavor deterioration inhibitor, and the like have also been proposed (Patent Document 3).

On the other hand, a deteriorated odor production inhibitor of citral-containing products that is characterized by containing epigallocatechin has been proposed as a method for inhibiting production of deteriorated odors of both p-methylacetophenone and p-cresol (Patent Document 4).

Moreover, a deteriorated odor production inhibitor of citral or citral-containing products that is characterized by containing at least one solvent extract selected from the group consisting of *Angelica keiskei*, Avocado, *Plantago asiatica*, semi-fermented tea leaves, fermented tea leaves, sicklepod and hawthorn, has been proposed (Patent Document 5).

Moreover, a flavor or aroma deterioration inhibitor containing theaflavin and analogues thereof as an active ingredient has been proposed (Patent Document 6).

Further, a flavor or aroma deterioration inhibitor containing a product obtained by treating a tea extract component with an oxidation enzyme as an active ingredient has also been proposed (Patent Document 7).

However, flavor or aroma deterioration of food and drinks, cosmetics, and the like is brought about by composite factors associated with numerous reactions such as oxidation, decomposition, isomerization, and polymerization of each component such as fats and oils, proteins, saccharides, amino acids, organic acids, contained in food and drinks, and cosmetics, in addition to as a result of the changes in flavor or aroma components themselves induced by oxygen, light, heat, and the like.

Therefore, even if the above prior art method is employed, the deterioration inhibition effect may still be inadequate, and a more effective deterioration inhibition technology has been desired.

Moreover, the deterioration inhibitors according to the above prior art may cause coloring of food and drinks, and cosmetics when they are used at concentrations exhibiting a sufficient effect, and therefore a deterioration inhibition technology that does not affect the color of food and drinks has been desired.

PRIOR ART DOCUMENT

Patent Document

Patent Document 1

Japanese Translation of PCT International Application Publication No. 2002-507887 A

Patent Document 2

Japanese Patent Laid-Open No. 2002-180081 A

Patent Document 3

Japanese Patent Laid-Open No. 2003-96486 A

Patent Document 4

Japanese Patent Laid-Open No. 2002-338990 A

Patent Document 5

Japanese Patent Laid-Open No. 2004-018613 A

Patent Document 6

Japanese Patent Laid-Open No. 2005-171116 A

Patent Document 7

International Publication No. WO 2009/011271 A

Non-Patent Document

Non-Patent Document 1

Patent Office Journal, Collection of Well-known Prior Arts (Fragrances), Part I, General Fragrances, Jan. 29, 1999, pages 141-147

Non-Patent Document 2

Peter Schieberle and Werner Grosch; J. Agric. Food Chem., Vol. 36, 797-800 (1988)

Non-Patent Document 3

The 57th Natural Organic Compounds Symposium Proceedings, P-33, 375-380 (2015)

SUMMARY OF INVENTION

Problem to be Solved by the Invention

The problem to be solved by the present invention is to provide a deterioration inhibitor that is more effective than the prior art with respect to flavor or aroma deterioration of food and drinks and cosmetics caused by complicated factors, while not affecting the color of food and drinks, and cosmetics.

Means for Solving Problem

The present inventors have found, as a result of detailed investigation on the deterioration of citral due to heating or an elapsed time and the inhibition method thereof, that an autoxidation product of theaflavin and analogues thereof has a remarkable effect on inhibiting production of p-cresol and p-methylacetophenone that are extremely strong deteriorated odor-causing substances derived from citral.

Moreover, the present inventors have also found that theanaphthoquinone and analogues thereof contained in the autoxidation product of theaflavin and analogues thereof is an active ingredient for inhibiting the deteriorated odor.

Furthermore, the present inventors have found that the naphthoquinone is effective not only for the deterioration of citral but also for the deterioration inhibition of carotenoids and have completed the present invention.

More specifically, the present invention is as follows.

[1] A flavor or aroma deterioration inhibitor comprising a theanaphthoquinone and analogues thereof as an active ingredient.

[2] The deterioration inhibitor, wherein the theanaphthoquinone and analogues thereof is a compound represented by the following formula (1) and the compound is any one or a combination of two or more thereof selected from a theanaphthoquinone wherein both substituents $R_1$ and $R_2$ are hydrogen in the formula, a theanaphthoquinone3'-O-gallate wherein substituent $R_1$ is a galloyl group and $R_2$ is hydrogen in the formula, a theanaphthoquinone3-O-gallate wherein substituent $R_1$ is hydrogen and $R_2$ is a galloyl group in the formula;

a theanaphthoquinone3,3'-di-O-gallate wherein both substituents $R_1$ and $R_2$ are galloyl groups in the formula.

[Chemical Formula 1]

(1)

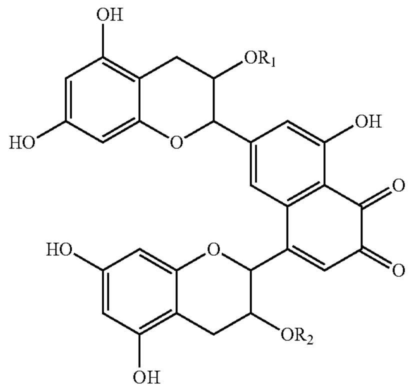

[3] The deterioration inhibitor, wherein the flavor or aroma is citrus flavor or aroma.

[4] The deterioration inhibitor, wherein the flavor or aroma is based on citral.

[5] A flavor or fragrance composition comprising a flavor or fragrance raw material and the deterioration inhibitor.

[6] An oral product comprising the deterioration inhibitor.

[7] An oral product comprising the flavor or fragrance composition.

[8] A cosmetic product comprising the deterioration inhibitor.

[9] A cosmetic product comprising the fragrance composition.

[10] A method for inhibiting flavor, flavor or aroma deterioration of a flavor or fragrance composition, an oral product or a cosmetic product by adding the deterioration inhibitor.

[11] The method for inhibiting deterioration, wherein an amount added is 0.0001 to 10 ppm as an active ingredient.

[12] The method for inhibiting deterioration, wherein flavor or aroma is citrus flavo or aroma.

[13] The method for inhibiting deterioration, wherein the flavor or aroma is based on citral.

[14] A method for inhibiting production of a deteriorated odor due to heat or an elapsed time of a flavor or fragrance composition, an oral product or a cosmetic product, comprising adding an effective amount of the deterioration inhibitor.

[15] The method for inhibiting production of a deteriorated odor, wherein the deteriorated odor is a deteriorated odor due to p-cresol or p-methylacetophenone.

[16] A method for producing theanaphthoquinone and analogues thereof, comprising autoxidizing theaflavin and analogues thereof.

[17] The method for producing theanaphthoquinone and analogues thereof, comprising autoxidizing theaflavin and analogues thereof in a 10 to 50% ethanol aqueous solution.

[18] The method for producing theanaphthoquinone and analogues thereof, comprising adjusting a pH of a reaction solution to 6 to 10.

[19] The method for producing theanaphthoquinone and analogues thereof, wherein an autoxidation reaction temperature is 10 to 50° C.

[20] The method for producing theanaphthoquinone and analogues thereof, comprising adding 0.1 to 3 parts by mass of an acidic substance with respect to 100 parts by mass of a reaction solution to adjust a pH of the reaction solution to 1 to 5 and stopping an oxidation reaction.

[21] The method for producing theanaphthoquinone and analogues thereof, wherein theaflavin and analogues thereof is theaflavin, theaflavin3-O-gallate, theaflavin3'-O-gallate, theaflavin3,3'-di-O-gallate or a combination of two or more thereof.

Effect of the Invention

By adding the deterioration inhibitor of the present invention to flavor or fragrance compositions, oral products such as food and drinks, and cosmetic products such as cosmetics, flavor or aroma deterioration due to heat and an elapsed time can be inhibited.

In particular, the deterioration inhibitor of the present invention has a remarkable effect on the deterioration of citral, inhibits the production of p-cresol and p-methylacetophenone that are deteriorated odor-causing substances derived from citral, and can maintain a fresh citral flavor or aroma.

Furthermore, the deterioration inhibitor of the present invention has a remarkable effect on the deterioration of carotenoids, inhibits the production of off-taste and off-odor (earthy odor, lipstick-like odor) due to the deterioration of carotenoids, and can maintain a fresh flavor or aroma.

Moreover, since the deterioration inhibitor of the present invention has a lower polyphenol content than the polyphenol-based antioxidant currently used as an aroma and flavor deterioration inhibitor for food products derived from natural products, it has little effect on the taste of the final product and can reduce bitter taste. Furthermore, precipitation and coloring thereof can be reduced.

Hereinafter, the present invention will be described in more detail.

<1> Deterioration Inhibitor

[1] Active Ingredient

Theanaphthoquinone and analogues thereof that is an active ingredient of the deterioration inhibitor of the present invention, is a compound in which the benzotropolone ring of theaflavin theaflavin and analogues thereof undergoes oxidization and changes to a naphthoquinone ring.

In the present invention, theanaphthoquinone and analogues thereof is a term indicating theanaphthoquinone, theanaphthoquinone3'-O-gallate, theanaphthoquinone3-O-gallate, theanaphthoquinone3,3'-O-gallate or a combination of two or more thereof.

Further, in the present invention, theaflavin and analogues thereof is a term indicating theaflavin, theaflavin3-O-gallate, theaflavin3'-O-gallate, theaflavin3,3'-di-O-gallate or a combination of two or more thereof.

Non-Patent Document 3 reports two types, theanaphthoquinone and theanaphthoquinone3'-O-gallate that are represented by the following formula (1) but does not suggest any effect of inhibiting flavor or aroma deterioration at all.

[Chemical Formula 2]

(1)

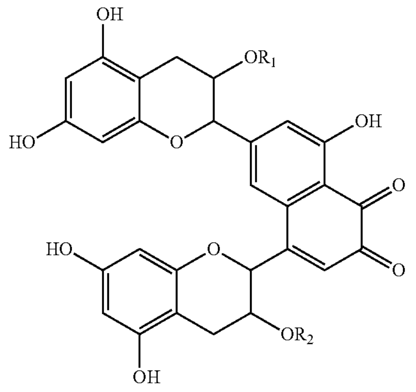

wherein, when both the substituents $R_1$ and $R_2$ are hydrogen, the above compound corresponds to theanaphthoquinone, and when the substituent $R_1$ is a galloyl group and the substituent $R_2$ is hydrogen, it corresponds to theanaphthoquinone3'-O-gallate.

[Chemical Formula 3]

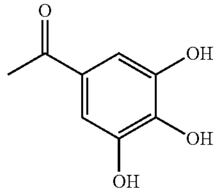

Galloyl group

The theanaphthoquinone and analogues thereof can be obtained by oxidizing a theaflavin and analogues thereof as described above and separating and purifying the obtained product. However, since the theanaphthoquinone and analogues thereof itself is susceptible to an oxidation reaction, and when applying an enzymatic oxidation reaction for example, the oxidation reaction proceeds too much and the theanaphthoquinone and analogues thereof is decomposed in many cases.

Therefore, when theanaphthoquinone and analogues thereof is obtained from theaflavin and analogues thereof by an oxidation reaction, an oxidation reaction under mild conditions such as an autoxidation reaction under weak acid to alkaline conditions, is preferably carried out.

[2] Raw materials

The theanaphthoquinone and analogues thereof used in the present invention can be easily obtained by oxidizing theaflavin and analogues thereof represented by the following formula (2), as described above.

[Chemical Formula 4]

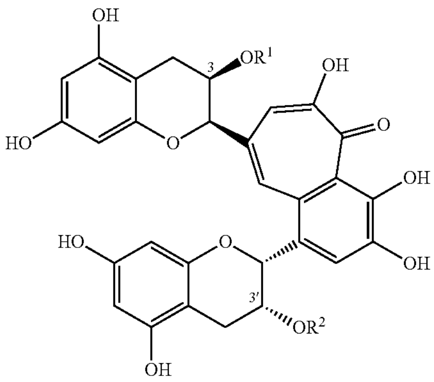

(2)

wherein $R_1$ and $R_2$ each independently represents hydrogen or a galloyl group.

Theaflavin and analogues thereof that is the raw material for that purpose, is a red pigment component produced from catechins in the fermentation process of tea (*Camellia sinensis*) leaves, and includes theaflavin where the substituents $R_1$ and $R_2$ are both hydrogen in the above formula (2), theaflavin3-O-gallate where the substituent $R_1$ is a galloyl group and $R_2$ is hydrogen in the above formula (2), theaflavin3'-O-gallate where the substituent $R_1$ is hydrogen and $R_2$ is a galloyl group in the above formula (2), theaflavin3, 3'-di-O-gallate where both substituents $R_1$ and $R_2$ are galloyl groups in the above formula (2), and the like.

The theaflavin and analogues thereof n that is commercially available can be used as it is, and those obtained as extracts from tea leaves can also be used.

The tea leaves used for extraction are not particularly limited, and among non-fermented tea (green tea), semi-fermented tea and fermented tea, fermented tea or semi-fermented tea leaves containing a large amount of theaflavin and analogues thereof are preferable.

Fermented tea is such that fresh leaves of tea are withered and rolled, and then completely fermented with its own oxidation enzyme. Semi-fermented tea is such that some of the catechins and the like of fresh leaves are fermented (oxidized) with its own oxidation enzyme when the fresh leaves are withered and agitated and has the degree of fermentation of 30 to 70%. The fermented tea used for extracting theaflavin and analogues thereof includes black tea, Pu-erh tea, and the like, and the semi-fermented tea includes oolong tea and the like, and black tea is particularly preferable.

[3] Oxidation Reaction Treatment

The method for oxidizing theaflavin and analogues thereof is not particularly limited, and ordinary oxidizing agents, oxidation enzymes, and the like are used, but as described above, the reaction often proceeds too much with the ordinary oxidizing agents, and milder autoxidation conditions are preferably employed.

Autoxidation of theaflavin and analogues thereof can be carried out by a method for blowing air into a theaflavin solution, a method for stirring a theaflavin and analogues thereof solution in an air atmosphere, or a method of combining them for use.

The solvent used for preparing the theaflavin and analogues thereof solution is water or a polar organic solvent, the organic solvent may be a hydrous, and the polar organic solvent includes alcohol, acetone, ethyl acetate, and the like. Among them, water or aliphatic alcohols having 2 to 4 carbon atoms, such as ethanol, propanol and butanol are preferred from the viewpoint of safety to the human body and facilitation of handleability, and in particular water or ethanol or a mixture thereof (1 to 95% ethanol aqueous solution) is desirable.

The amount of solvent used in the reaction can be arbitrarily selected, but in general the amount of solvent is 5 to 1000 parts by mass with respect to 1 part by mass of theaflavin and analogues thereof.

The oxidation reaction can be accelerated by adjusting the pH of the theaflavin and analogues thereof solution to 6 to 10 by addition of a basic substance. The basic substance includes sodium or potassium salts of citric acid and phosphoric acid, and the like, and trisodium citrate or disodium hydrogen phosphate is particularly preferable.

The amount of the basic substance added depends on the type of the basic substance, but in the case of disodium hydrogen phosphate, it is added in an amount of 0.01 to 1 parts by mass and preferably 0.05 to 0.3 parts by mass with respect to 100 parts by mass of the theaflavin and analogues thereof solution.

There can be exemplified a method where the reaction temperature is in the range of about 0 to 90° C., preferably about 10 to 50° C., and the reaction time is about 5 minutes to 48 hours, preferably about 10 minutes to 6 hours.

Further, after the oxidation reaction, the reaction is preferably terminated by adding an acidic substance and adjusting the pH to 1 to 5. The acidic substance to be added includes citric acid, phosphoric acid, and the like, and citric acid is particularly preferable.

The amount of the acidic substance added depends on the type of the acidic substance, but in the case of citric acid, it is 0.01 to 5 parts by mass and preferably 0.1 to 3 parts by mass with respect to 100 parts by mass of the theaflavin and analogues thereof solution.

[4] Purification Treatment

The solution obtained by the above autoxidation reaction can be further subjected to purification treatment such as decolorization and deodorization and can be utilized.

For the purification treatment, a synthetic resin adsorbent composed of activated carbon, alumina, silica gel or a porous styrene-divinylbenzene copolymer, a methacrylic acid ester-based porous polymer resin, a gel-type synthetic adsorbent, and the like can be used.

The synthetic resin adsorbent for purification includes such as "Diaion HP-20 (product name)" and "Diaion SP-70 (product name)", manufactured by Mitsubishi Chemical Co., Ltd., "Amberlite XAD-2 (product name)", manufactured by Organo Corporation, "Sephadex LH-20 (product name)", manufactured by GE Healthcare Japan Co., Ltd., and the like can be used.

Moreover, treatment with two or more of synthetic adsorbents selected from the above group may be combined for use.

[5] Formulation

The obtained theanaphthoquinone and analogues thereof can be directly contained as the deterioration inhibitor in flavor or fragrance compositions, oral products, cosmetic products, and the like, and can also be formulated as follows and used.

For example, the obtained theanaphthoquinone is dissolved in a (mixed) solvent such as water, alcohol, glycerin, propylene glycol, and the like at an appropriate concentration (specifically, a mixed solvent such as water/ethanol, water/ethanol/glycerin, water/glycerin, and the like) to prepare a liquid formulation.

Alternatively, dextrin, sucrose, pectin, chitin, and the like can be added, and these can be further concentrated into a paste.

Moreover, an excipient (dextrin and the like) can be added to each solution and the obtained solution can be spray dried to be formed into powder. Further, by adding the liquid formulation together with an emulsifier to an oil or fat, and the like and dispersing the mixture, an oil-soluble liquid formulation can be obtained, and various dosage forms can be adopted depending on the application.

Moreover, the product of the theaflavin and analogues thereof oxidation reaction described above can also be used as a crude product without passing through a purification step. In that case, the theanaphthoquinone and analogues thereof as an active ingredient is preferably contained in an amount of 1% by mass or more as the solid content in the crude product. When the content of theanaphthoquinone and analogues thereof is less than 1% by mass, the deterioration inhibition effect may not be sufficient, and the flavor or fragrance compositions, oral products and cosmetic products may be colored due to the influence of impurities contained in the crude product.

[6] Addition Amount

The deterioration inhibitor of the present invention can be appropriately added in the production process of flavor or fragrance compositions, oral products, cosmetic products, and the like. The amount added varies depending on the type of the object to be added, but an amount of 0.0001 to 10 ppm as an active ingredient is appropriate for flavor or fragrance compositions, oral products, cosmetic products, and the like.

When the target product is an oral product such as food or drinks, the deterioration inhibitor of the present invention is used in an amount of preferably 0.001 to 1 ppm, more preferably 0.01 to 0.5 ppm, and most preferably 0.02 to 0.2 ppm from the viewpoint of having almost no effect on the original flavor of food and drinks.

If the amount added is less than 0.0001 ppm, the deterioration inhibition effect may not be sufficient, and if the amount added exceeds 10 ppm, an off-taste may be felt.

[7] Additional components

Further, for the purpose of enhancing the flavor deterioration inhibition effect, the deterioration inhibitor of the present invention and a transition metal ion such as an iron ion can be combined for use, and in particular an iron ion is preferable from the viewpoint of safety to the human body.

The iron ion source is not particularly restricted, and metallic iron, iron salts, heme iron, and the like can be used. Specifically, the iron ion source includes iron chloride, iron citrate, iron gluconate, iron lactate, iron pyrophosphate, iron sulfate, heme iron, and the like.

Moreover, in order to enhance the deterioration inhibition ability, antioxidants, such as L-ascorbic acid, enzyme-treated rutin, a *Sophora japonica* extract, a grape seed extract, a rosemary extract, a green tea extract, and the like which are generally used with the deterioration inhibitor of the present invention can be appropriately contained.

Furthermore, in order to prevent coloring caused by the reaction between a metal and a substrate, and the like, the deterioration inhibitor of the present invention can be mixed with a metal sequestering agent, such as citric acid, gluconic acid, tartaric acid, phytic acid, pyrophosphate, and polyphosphoric acid.

<2> Flavor or Aroma that is Subject to Deterioration Inhibition

As used herein, the flavor refers to a combination of a smell felt by the sense of smell of oral products such as food and drinks and a taste felt in the portion extending from the oral cavity to the nasal cavity. The flavor includes both a flavor originally possessed by the oral product such as food and drinks and a flavor imparted to the oral product by adding a flavor composition. The aroma is a smell that is imparted by adding a fragrance composition to cosmetic products and the like and is mainly perceived by the sense of smell.

The deterioration inhibitor of the present invention is effective for deterioration of various aromas and flavors and is particularly effective for deterioration of citrus aroma and flavor.

In particular, the deterioration inhibitor of the present invention is effective for deterioration of the aroma and flavor based on citral and has a prominent effect of inhibiting the production of p-methylacetophenone (cinnamon odor) and p-cresol (chemical odor), which are extremely strong deteriorated odor-causing substances derived from citral.

Furthermore, the deterioration inhibitor of the present invention is remarkably effective for the deterioration of carotenoid and can inhibit the production of off-tastes and off-odors (earthy odor, lipstick-like odor) due to the deterioration of carotenoid.

<3> Applicable Target of Deterioration Inhibitor

The deterioration inhibitor of the present invention can be used in oral products, flavor or fragrance compositions, cosmetic products, and the like without particular limitation, and specific examples thereof include the following.

[1] Oral Products

The oral product referred to in the present invention specifically refers to food and drinks and oral care products (oral hygiene agents for keeping the teeth and the inside of the mouth clean).

Examples of oral products include beverages, confectioneries, fats and oils and processed fats and oils, milk, dairy products, oral hygiene agents, and the like. More specifically, the following can be included.

Examples of beverages include coffee, black tea, soft drinks, lactic fermenting beverages, fruit-free beverages, fruit-containing beverages, vegetable beverages, nutritional drinks, and the like, and in particular citrus-based carbonated beverages, fruit juices, fruit juice beverages, vegetable beverages, lactic drinks, tea drinks, and the like are preferred.

Examples of confectioneries include jellies, puddings, bavarois, candies, biscuits, cookies, chocolates, cakes, and the like, and in particular citral-containing yogurt, jelly, frozen desserts such as ice cream, candies, candy confectioneries, gum and the like are preferred.

Examples of fats and oils and processed fats and oils include edible fats and oils (animal fats and oils, vegetable fats and oils), margarine, shortening, mayonnaise, dressings, hard butter and the like, and further include instant (fried) noodles, deep-fried tofu (a fried tofu, such as a deep-fried thin tofu, a deep-fried thick tofu, a deep-fried tofu mixed with thinly sliced vegetables), deep-fried kamaboko, tempura, fry, snacks (potato chips, fried crackers, fried dough cakes, doughnuts), cooked frozen food (frozen croquette, fried shrimp and the like).

Examples of milk, dairy products, and the like include raw milk, milk, processed milk, and the like as milk, and cream, butter, butter oil, concentrated whey, cheese, condensed milk, powdered milk, concentrated milk, and the like as dairy products.

Examples of oral hygiene agents include toothpaste, mouthwash, a mouth refreshing agent, a halitosis inhibitor, and the like.

[2] Flavor or Fragrance Composition

Examples of flavor or fragrance compositions include flavor compositions for food and drinks, such as various flavors and food materials, and fragrance compositions for cosmetic products, which all comprise flavor or fragrance raw materials (refined oil, essence, concrete, absolute, extract, oleoresin, resinoid, recovered flavor, carbon dioxide extract, synthetic flavor and the like), and are particularly suitable for citrus-based flavors comprising citral.

[3] Cosmetic Products

Cosmetic products refer to cosmetics that are skin care products and makeup products, as well as perfumes containing large amounts of fragrances.

Examples of cosmetic products include perfumes, cosmetics, detergents, soaps, shampoos, rinses, bath salts, aromatics, and the like, and are particularly suitable for cosmetic products having a citrus smell containing citral (Non-Patent Document

EXAMPLES

The present invention will be specifically described below with reference to examples, but the present invention is not limited to the description of the Examples.

Production Example 1

To 3.9 g of theaflavin and analogues thereof containing composition ("Theaflavin TF40 (trade name)" containing 40% of theaflavin and analogues thereof, manufactured by Yaizu Suisankagaku Industry Co., Ltd.), 600 g of a 30% ethanol aqueous solution and 0.8 g of disodium hydrogen phosphate were added (pH 7.7), the mixture was stirred at 20° C. for 2.5 hours, and then 2.3 g of citric acid was added (pH 3.7).

The solution was concentrated under reduced pressure and then freeze-dried to obtain 7 g of brown powder (containing 3.9 g of a "crude product of theanaphthoquinone and analogues thereof").

Next, 5 g of the above powder (containing 2.8 g of a "crude product of theanaphthoquinone and analogues thereof") was purified by open column chromatography and high performance liquid chromatography to obtain 48 mg of theanaphthoquinone.

Production Example 2

A "black tea leaf extract" was prepared based on the description of "Extraction Example 4" in Patent Document 5 of existing technology.

1000 g of a 95% ethanol aqueous solution was added to 50 g of black tea leaves, and the mixture was heated under reflux for 1 hour for extraction. After removing the insoluble substances by filtration, 5 g of activated carbon was added to the filtrate and the mixture was stirred at room temperature for 1 hour.

Activated carbon was removed by filtration and then the filtrate was concentrated under reduced pressure.

Subsequently, the concentrate was freeze-dried to obtain 10.3 g of brown powder (hereinafter referred to as "black tea leaf extract").

Production Example 3

A "oxidation enzyme-treated tea extract" was prepared based on the description of "Extraction Example 1" in Patent Document 7 of existing technology.

2000 g of water was added to 100 g of dried green tea leaves, and the mixture was heated under reflux for 1 hour. After removing the insoluble substances by filtration, 0.04 g of laccase ("Laccase Y120 (trade name)" manufactured by Amano Enzyme Co., Ltd.) was added to the filtrate (solid content of 1.5 to 2.5%), and the mixture was reacted at 55° C. for 4 hours.

After concentrating this enzyme-treated solution, 300 g of a 95% ethanol aqueous solution was added, and the mixture was heated under reflux for 30 minutes to carry out enzyme inactivation treatment. After cooling the reaction solution to −15° C., the insoluble substances were removed by filtration, and the filtrate was concentrated under reduced pressure and freeze-dried to obtain 16.5 g of a dark brown powder (hereinafter referred to as "oxidation enzyme-treated tea extract").

Test Example 1

Quantification of Theanaphthoquinone and Analogues Thereof

Theaflavin and analogues thereof containing composition (Theaflavin TF40) that was a raw material of the active ingredient of the present invention, the crude product of theanaphthoquinone and analogues thereof containing the active ingredient of the present invention, theanaphthoquinone that was the active ingredient of the present invention, the black tea leaf extract and oxidation enzyme-treated tea extract that were products of existing technology, were each subjected to measurement of a theanaphthoquinone and analogues thereof content with high-speed liquid chromatography under the following measurement conditions.

Apparatus: "G1312B HPLC system" manufactured by Agilent Technologies Inc.

Column: "CAPCELL PAK (Registered Trademark)" C18 MG, 4.6 mm I.D.×250 mm, manufactured by Osaka Soda Co., Ltd.

Column temperature: 40° C.

Eluent: A. Acetonitrile

B. Water

| Gradient condition | | | | | |
|---|---|---|---|---|---|
| | 0 min.→ | 10 min.→ | 14.5 min.→ | 23.5 min.→ | 25 min. |
| A. Acetonitrile | 10% | 11.35% | 31.15% | 32.05% | 100% |
| B. Water | 90% | 88.65% | 68.85% | 67.95% | 0% |

Flow speed: 1 ml/minute

Table 1 shows the content of each theanaphthoquinone and analogues thereof.

TABLE 1

| Measurement results of theanaphthoquinone and analogues thereof contents | | |
|---|---|---|
| Objects to be measured | Theanaphthoquinone | Theanaphthoquinone-3'-gallate |
| Theaflavin and analogues thereof containing composition (Theaflavin TF40) | Not detected | Not detected |
| Crude product of theanaphthoquinone and analogues thereof | 1.71% | 1.84% |
| Theanaphthoquinone | 100% | Not detected |
| Black tea leaf extract | Not detected | Not detected |
| Oxidation enzyme-treated tea extract | Not detected | Not detected |

As shown in Table 1, the product of the present invention was found to contain theanaphthoquinone and analogues thereof not contained in the theaflavin and analogues thereof, black tea leaf extract, and oxidation enzyme-treated tea extract, which were obtained by prior art.

Test Example 2

The theanaphthoquinone of the present invention and theaflavin and analogues thereof containing composition (Theaflavin TF40) that was the raw material of the present invention, and black tea leaf extract and oxidation enzyme-treated tea extract that were products of existing technology, were evaluated for inhibition effect on production of p-cresol and p-methylacetophenone.

An acidic citral solution was prepared by adding citral to a buffer solution of pH 3.0 prepared with 1/10 M citric acid-1/5 M disodium hydrogen phosphate so as to have a concentration of 10 ppm of citral.

To this solution, each of the theanaphthoquinone of the present invention, theaflavin and analogues thereof containing composition (Theaflavin TF40) that was a raw material of the present invention, black tea leaf extract and oxidation enzyme-treated tea extract that were products of existing technology, was added to each concentration in Table 2, and 18 g thereof each was packed in a glass vial of 20 ml volume (with a polytetrafluoroethylene cap).

Each vial was stored in a thermostatic bath (50° C.) for 7 days, and the amounts of p-cresol and p-methylacetophenone produced in each acidic citral solution were measured by high performance liquid chromatography under the following measurement conditions.

Apparatus: "G1312B HPLC system" manufactured by Agilent Technologies Inc.

Column: "CAPCELL PAK (Registered Trademark)" C18 MG, 4.6 mm I.D.×250 mm, manufactured by Osaka Soda Co. Ltd.

Column temperature: 40° C.

Eluent: A. Acetonitrile

B. Water

| Gradient condition | | | |
|---|---|---|---|
| | 0 min.→ | 25 min.→ | 26 min. |
| A. Acetonitrile | 10% | 100% | 100% |
| B. Water | 90% | 0% | 0% |

Flow speed: 1 ml/minute

For comparison, an acidic citral solution without addition of the product of the present invention was prepared, refrigerated for 7 days and stored at 50° C., and then measured in the same manner. Subsequently, relative values of amounts of p-cresol and p-methylacetophenone produced were determined with the amounts of p-cresol and p-methylacetophenone produced in the product without the addition, stored at 50° C. for 7 days, being as 100, respectively. The results are shown in Table 2.

TABLE 2

| Measurement results of amounts (%) of p-cresol and p-methylacetophenone produced | | | |
|---|---|---|---|
| Additives | Temperature | p-Cresol | p-Methylacetophenone |
| Additive-free | Refrigeration | 0 | 0 |
| Additive-free | 50° C. | 100 | 100 |
| Theanaphthoquinone 10 ppb | 50° C. | 96 | 100 |
| Theanaphthoquinone 20 ppb | 50° C. | 76 | 82 |
| Theanaphthoquinone 40 ppb | 50° C. | 61 | 54 |
| Theanaphthoquinone 100 ppb | 50° C. | 24 | 22 |
| Theanaphthoquinone 200 ppb | 50° C. | 16 | 8 |
| Theaflavin and analogues thereof containing composition (Theaflavin TF40) 320 ppb | 50° C. | 86 | 62 |
| Theaflavin and analogues thereof containing composition (Theaflavin TF40) 640 ppb ppb | 50° C. | 66 | 40 |
| Black tea leaf extract 5 ppm | 50° C. | 92 | 20 |
| Oxidation enzyme-treated tea extract 2 ppm | 50° C. | 99 | 72 |

From the results in Table 2, it was found that the theanaphthoquinone of the present invention significantly inhibited the production of deteriorated odor, and the effect was remarkable at a concentration of 20 to 200 ppb.

Test Example 3

The crude product of theanaphthoquinone and analogues thereof of the present invention, theaflavin and analogues thereof containing composition (Theaflavin TF40) that was a raw material of the present invention, and black tea leaf extract and oxidation enzyme-treated tea extract that were products of existing technology, were evaluated for inhibition effect on production of p-cresol and p-methylacetophenone in the same manner.

Purified water was added to 80 g of granulated sugar, 0.8 g of citric acid, 0.4 g of sodium citrate, and 1 g of a 1% citral solution to adjust the total amount to 1000 g. To this solution, each of the crude product of theanaphthoquinone and analogues thereof of the present invention, the theaflavin and analogues thereof containing composition (Theaflavin TF40) that was the raw material of the present invention, and the black tea leaf extract and oxidation enzyme-treated tea extract that were products of existing technology, was added to each concentration shown in Table 3, the mixture was sterilized at 70° C. for 10 minutes, and then filled in a can to prepare a lemon-tasted beverage.

The above lemon beverages were each stored at 50° C. for 7 days in a thermostatic bath, and the amounts of p-cresol and p-methylacetophenone produced in each lemon-tasted beverage were measured by high performance liquid chromatography.

For comparison, a lemon beverage without addition of the product of the present invention was prepared, refrigerated for 7 days and stored at 50° C., and then measured in the same manner. Subsequently, relative values of amounts of p-cresol and p-methylacetophenone produced were determined with the amounts of p-cresol and p-methylacetophenone produced in the product without the addition, stored at 50° C. for 7 days, being as 100, respectively. The results are shown in Table 3.

TABLE 3

Amounts of p-cresol and p-methylacetophenone produced

| Additives | Temperature | p-Cresol | p-Methylacetophenone |
|---|---|---|---|
| Additive-free | Refrigeration | 0 | 0 |
| Additive-free | 50° C. | 100 | 100 |
| Crude product of theanaphthoquinone and analogues thereof 320 ppb | 50° C. | 61 | 28 |
| Crude product of theanaphthoquinon and analogues thereof e 640 ppb | 50° C. | 21 | 11 |
| Theaflavin and analogues thereof containing composition (Theaflavin TF40) 320 ppb | 50° C. | 81 | 57 |
| Theaflavin and analogues thereof containing composition (Theaflavin TF40) 640 ppb ppb | 50° C. | 54 | 38 |
| Black tea leaf extract 5 ppm | 50° C. | 84 | 30 |
| Oxidation enzyme-treated tea extract 2 ppm | 50° C. | 87 | 43 |

From the results in Table 3, it was found that by adding the product of the present invention containing a crude product of theanaphthoquinone and analogues thereof to the lemon-tasted beverage, the amounts of p-cresol and p-methylacetophenone produced were significantly reduced as compared with those of the products with the added theaflavin and analogues thereof containing composition (Theaflavin TF40) containing no theanaphthoquinone and analogues thereof, the added black tea leaf extract, and the added oxidation enzyme-treated tea extract.

Test Example 4

The lemon-tasted beverage of Test Example 3 was subjected to organoleptic evaluation with eight proficient panelists. Control lemon-tasted beverages that were a refrigerated product without addition of the product of the present invention (evaluation score set to 1 point) and a product stored at 50° C. for 7 days without addition of the product of the present invention (evaluation score set to 5 points), were used, and the degree of deterioration of the flavor was evaluated for each lemon-tasted beverage. The results are shown in Table 4.

It is noted that the average organoleptic evaluation scores shown in Table 4 are the average values scored in each panel as ranked according to the following criteria.

The scoring criteria are based on the following evaluation criteria for the off-taste and off-odor (p-cresol-like (chemical odor), p-methylacetophenone-like (cinnamon odor)).

Very strong perception: 5 points

Strong perception: 4 points

Perceivable: 3 points

Weak perception: 2 points

Not perceivable: 1 point

Test Example 5

The degree of coloring was evaluated for each lemon-tasted beverage of Test Example 4. The degree of coloring was defined as an absorbance at a wavelength of 450 nm for each lemon beverage, and the results are shown in Table 4.

TABLE 4

Evaluation results of organoleptic evaluation and coloring for off-taste and off-odor

| Additives | Temperature | p-Cresol-like | p-Methylacetophenone-like | Degree of coloring (abs. 450 nm) | Degree of coloring (visually) |
|---|---|---|---|---|---|
| Additive-free | Refrigeration | 1 | 1 | 0.0215 | No coloring |
| Additive-free | 50° C. | 5 | 5 | 0.0294 | No coloring |
| Crude product of theanaphthoquinone and analogues thereof 320 ppb | 50° C. | 3 | 3 | 0.0352 | No coloring |
| Crude product of theanaphthoquinone and analogues thereof 640 ppb | 50° C. | 2 | 2 | 0.0461 | Coloring |

TABLE 4-continued

| Evaluation results of organoleptic evaluation and coloring for off-taste and off-odor | | | | | |
|---|---|---|---|---|---|
| Additives | Temperature | p-Cresol-like | p-Methylacetophenone-like | Degree of coloring (abs. 450 nm) | Degree of coloring (visually) |
| Black tea leaf extract 5 ppm | 50° C. | 3 | 3 | 0.0493 | Coloring |
| Oxidation enzyme-treated tea extract 2 ppm | 50° C. | 4 | 4 | 0.0332 | No coloring |

From the results in Table 4, by adding the crude product of theanaphthoquinone and analogues thereof of the present invention to the lemon-tasted beverage, the deteriorated odors of p-cresol and p-methylacetophenone-like odor were found to be remarkably inhibited as compared with those of the black tea leaf extract and the oxidation enzyme-treated tea extract, and the crude product of theanaphthoquinone and analogues thereof exhibited the above effect at a concentration that did not affect the color of the beverage.

Test Example 6 (Lotion)

A lotion was prepared by a routine procedure, compounding the following components in the prescribed amounts below.

| | |
|---|---|
| 1,3-butylene glycol | 60.0 g |
| Glycerin | 40.0 g |
| Oleyl alcohol | 1.0 g |
| POE (20) sorbitan monolauric acid ester | 5.0 g |
| POE (15) lauryl alcohol ether | 5.0 g |
| 95% ethanol | 100.0 g |
| Methylparaben | 1.0 g |
| Gardenia yellow pigment | 0.1 g |
| Purified water | 783.9 g |

To 1,000 g of the model base described above, 2.0 g of lemon fragrance, and each of the crude product of theanaphthoquinone and analogues thereof of the present invention, theaflavin and analogues thereof containing composition (Theaflavin TF40) which was the raw material of the present invention, black tea leaf extract and the oxidation enzyme-treated tea extract that were products of existing technology, were added to each concentration shown in Table 5 and stored at 50° C. for 7 days in a thermostatic bath.

Each of the obtained mixture was subjected to organoleptic evaluation by ten proficient panelists.

For comparison, a refrigerated product without addition of the product of the present invention (evaluation score set to 1 point) and a product stored at 50° C. for 7 days without addition of the product of the present invention (evaluation score set to 5 points), were used, and each lotion was evaluated for the degree of deterioration of the lotion smell. The results are shown in Table 5.

Incidentally, the average organoleptic evaluation scores in Table 5 are average values scored in each panel according to the following criteria. The scoring criteria are based on the following evaluation criteria for the off-taste and off-odor (p-cresol-like (chemical odor), p-methylacetophenone-like (cinnamon odor)).

Very strong perception: 5 points
Strong perception: 4 points
Perceivable: 3 points
Weakly perception: 2 points
Not perceivable: 1 point

TABLE 5

| Evaluation results of heating test of lotion | | |
|---|---|---|
| Additives | Temperature | Organoleptic evaluation average score |
| Additive-free | Refrigeration | 1.0 |
| Additive-free | 50° C. | 5.0 |
| Theaflavin and analogues thereof-containing composition (Theaflavin TF40) 640 ppb | 50° C. | 1.7 |
| Crude product of theanaphthoquinone and analogues thereof 640 ppb | 50° C. | 1.3 |
| Black tea leaf extract 5 ppm | 50° C. | 1.9 |
| Oxidation enzyme-treated tea extract 2 ppm | 50° C. | 2.1 |

From the results in Table 5, it was found that by adding the crude product of theanaphthoquinone and analogues thereof of the present invention to the lotion, the deteriorated odors of the p-cresol and p-methylacetophenone-like odors were remarkably inhibited as compared with those of the products with the added theaflavin and analogues thereof containing composition (Theaflavin TF40) containing no theanaphthoquinone and analogues thereof, the added black tea leaf extract, and the added oxidation enzyme-treated tea extract.

Test Example 7 (Vegetable Juice Beverage)

Distilled water was added to 84 g of carrot turbid juice (36° Bx) and 86 g of orange concentrated fruit juice (64° Bx) to adjust the total amount to 1000 g. To this mixture each of the crude product of theanaphthoquinone and analogues thereof of the present invention, the black tea leaf extract and the oxidation enzyme-treated tea extract that were products of existing technology, was added to the respective concentrations shown in Table 6, and each mixture was filled in a glass container, sterilized at 90° C. for 30 minutes to prepare a vegetable juice beverage.

The obtained vegetable juice beverage was subjected to organoleptic evaluation by 6 experienced panelists. Control vegetable juice beverages that were the unsterilized product (evaluation score set to 1 point) and the sterilized product without addition of the product of the present invention (evaluation score set to 5 points) were used, and the degree of deterioration of the flavor of each vegetable juice beverage was evaluated. The results are shown in Table 6.

It is noted that the average organoleptic evaluation scores in Table 6 are average values scored in each panel according to the following criteria.

The scoring criteria are based on the following evaluation criteria for the off-taste and off-odor (earthy odor, lipstick-like odor) generated due to deterioration of carotenoids.

Very strong perception: 5 points

Strong perception: 4 points

Perceivable: 3 points

Weak perception: 2 points

Not perceivable: 1 point

TABLE 6

Organoleptic evaluation results of heating test of vegetable juice beverages

| Additives | Sterilization temperature | Organoleptic evaluation average score (off-odor) | Organoleptic evaluation average score (off-taste) |
|---|---|---|---|
| Non-sterilization | — | 1.0 | 1.0 |
| Additive-free | 90° C. | 5.0 | 5.0 |
| Crude product of theanaphthoquinone and analogues thereof 1.3 ppm | 90° C. | 2.6 | 3.0 |
| Crude product of theanaphthoquinone and analogues thereof 3.2 ppm | 90° C. | 2.3 | 2.5 |
| Black tea leaf extract 5 ppm | 90° C. | 3.3 | 3.3 |
| Oxidation enzyme-treated tea extract 2 ppm | 90° C. | 3.2 | 3.6 |

From the results in Table 6, it was found that by adding the crude product of theanaphthoquinone and analogues thereof of the present invention to each vegetable juice beverage, the deteriorated odors of the earthy odor and the lipstick-like odor generated due to the deterioration of carotenoids were remarkably inhibited as compared with those of the black tea leaf extract and the oxidation enzyme-treated tea extract.

INDUSTRIAL APPLICABILITY

By using the theanaphthoquinone and analogues thereof of the present invention in citral or the product containing citral, the production of deteriorated odors derived from citral due to change with time or due to heat can be effectively inhibited while the color of food and drinks, cosmetics, and the like is not affected.

Furthermore, the theanaphthoquinone and analogues thereof of the present invention has a remarkable effect on the deterioration of carotenoids and can inhibit the production of off-taste and off-odor (earthy odor, lipstick-like odor) due to the deterioration of carotenoids.

Thus, use of the deteriorated odor production inhibitor of the present invention efficiently inhibits the production of deteriorated odor that gradually progresses at each stage of the production, distribution, and storage period in the oral product, and maintains the fresh feeling, which thereby can maintain the quality of the product inexpensively and stably for a long period of time.

The invention claimed is:

1. A composition having a flavor or aroma deterioration inhibition effect, comprising:

a theanaphthoquinone, wherein both $R_1$ and $R_2$ are hydrogen in the formula (1), a theanaphthoquinone3'-O-gallate, wherein $R_1$ is a galloyl group and $R_2$ is hydrogen in the formula (1), a theanaphthoquinone3-O-gallate, wherein $R_1$ is hydrogen and $R_2$ is a galloyl group in the formula (1), and a theanaphthoquinone3,3'-di-O-gallate, wherein $R_1$ and $R_2$ are galloyl groups in the formula (1)

(1)

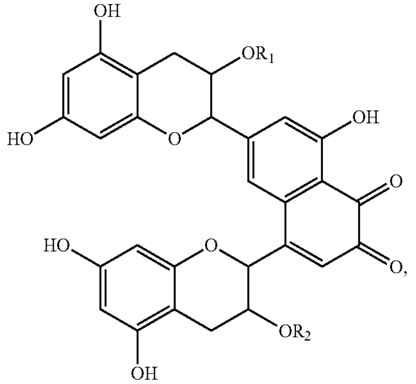

wherein the composition is produced by a method comprising autoxidizing theaflavin and analogues thereof in a 10 to 50% ethanol aqueous solution, and thereafter stopping the autoxidation reaction by adding 0.1 to 3 parts by mass of an acidic substance with respect to 100 parts by mass of the reaction solution to adjust a pH of the reaction solution to 1 to 5, wherein the autoxidation reaction is conducted at a temperature of 10 to 50° C.

2. The composition according to claim 1, wherein the flavor or aroma is citrus flavor or aroma.

3. The composition according to claim 1, wherein the flavor or aroma is based on citral.

4. A citrus-based flavor or fragrance composition comprising a citrus-based flavor or fragrance containing citral and the composition according to claim 1.

5. An oral product comprising the citrus-based flavor or fragrance composition according to claim 4.

6. A cosmetic product having a citrus flavor or fragrance, comprising the composition according to claim 1.

7. A cosmetic product comprising the citrus-based fragrance composition according to claim 4.

8. The composition according to claim 1, wherein the pH of the reaction solution during the autoxidation reaction is adjusted to 6 to 10.

9. The composition according to claim 1, theaflavin and analogues thereof comprising theaflavin, theaflavin3-O-gallate, theaflavin3'-O-gallate, and theaflavin3,3'-di-O-gallate.

10. A method for inhibiting flavor or aroma deterioration of a fragrance composition, an oral product or a cosmetic product comprising adding the composition according to claim 1 to a fragrance composition, an oral product or a cosmetic product.

11. The method for inhibiting deterioration according to claim 10, wherein the composition is added in an amount of 0.0001 to 10 ppm as an active ingredient.

12. The method for inhibiting deterioration according to claim 10, wherein the flavor or aroma is citrus flavor or aroma.

13. The method for inhibiting deterioration according to claim 10, wherein the flavor or aroma is based on citral.

14. A method for inhibiting production of a deteriorated odor due to heat or with time of a flavor or fragrance composition, an oral product or a cosmetic product, comprising adding an effective amount of the composition according to claim 1 to a flavor or fragrance composition, an oral product or a cosmetic product.

15. The method for inhibiting production of a deteriorated odor according to claim 14, wherein the deteriorated odor is a deteriorated odor due to p-cresol or p-methylacetophenone.

* * * * *